(12) United States Patent
Kanda et al.

(10) Patent No.: US 11,375,964 B2
(45) Date of Patent: Jul. 5, 2022

(54) ACQUISITION METHOD, ACQUISITION DEVICE, AND CONTROL PROGRAM FOR TOMOGRAPHIC IMAGE DATA BY MEANS OF ANGULAR OFFSET

(71) Applicants: RIKEN, Wako (JP); Nissan Chemical Corporation, Tokyo (JP)

(72) Inventors: Naohiro Kanda, Wako (JP); Takaoki Takanashi, Wako (JP)

(73) Assignees: RIKEN, Saitama (JP); Nissan Chemical Corporation, Tokyo (JP)

( * ) Notice: Subject to any disclaimer, the term of this patent is extended or adjusted under 35 U.S.C. 154(b) by 0 days.

(21) Appl. No.: 17/059,007

(22) PCT Filed: May 28, 2019

(86) PCT No.: PCT/JP2019/021165
§ 371 (c)(1),
(2) Date: Nov. 25, 2020

(87) PCT Pub. No.: WO2019/230741
PCT Pub. Date: Dec. 5, 2019

(65) Prior Publication Data
US 2021/0228167 A1     Jul. 29, 2021

(30) Foreign Application Priority Data

May 28, 2018  (JP) .............................. JP2018-101220

(51) Int. Cl.
*A61B 6/03*   (2006.01)
*G06T 11/00*  (2006.01)
*A61B 6/00*   (2006.01)

(52) U.S. Cl.
CPC ............ *A61B 6/4241* (2013.01); *A61B 6/032* (2013.01); *A61B 6/5205* (2013.01); *G06T 11/008* (2013.01)

(58) Field of Classification Search
CPC ..... A61B 6/4241; A61B 6/032; A61B 6/5205; G06T 11/008
See application file for complete search history.

(56) References Cited

U.S. PATENT DOCUMENTS 4,176,279 A * 11/1979 Schwierz ............... A61B 6/027
378/19
5,068,882 A * 11/1991 Eberhard ............... A61B 6/027
378/4

(Continued)

FOREIGN PATENT DOCUMENTS

CN     104899827 A    9/2015
JP     S63125242 A    5/1988

(Continued)

OTHER PUBLICATIONS

Arcadu et al., "A Forward Regridding Method with Minimal Oversampling for Accurate and Efficient Iterative Tomographic Algorithms," IEEE Transaction on Image Processing, 2016, vol. 25 (3), pp. 1207-1218.

(Continued)

*Primary Examiner* — Blake C Riddick
(74) *Attorney, Agent, or Firm* — Seed IP Law Group LLP

(57) ABSTRACT

In an embodiment of the present disclosure, in order to raise the reproducibility of a reconstructed tomographic image without increasing a calculation load, any one among two directions adjacent to two boundaries that demarcate an angular scan range is offset from any one among coordinate axes of a two-dimensional tomographic image of N pixels×N pixels, and the angle of the offset is made to be above 0 degrees and under 90 degrees or above −90 degrees and under 0 degrees. A detection device, which includes N detection elements, performs detection in each detection direction, and a first vector having N×N elements is obtained from a detection signal obtained by the detection device in (Continued)

a detection operation. A discrete Inverse Radon transform matrix is applied to the first vector to obtain a second vector having N×N elements. The second vector is de-vectorized to obtain image data for a two-dimensional tomographic image of N pixels×N pixels. An inverse matrix of a system matrix for an offset is obtained and used as the discrete Inverse Radon transform matrix.

15 Claims, 12 Drawing Sheets

(56) References Cited

U.S. PATENT DOCUMENTS

| | | | | |
|---|---|---|---|---|
| 5,187,659 | A * | 2/1993 | Eberhard | A61B 6/032 378/15 |
| 5,333,164 | A * | 7/1994 | Tam | G01N 23/046 378/14 |
| 5,341,460 | A * | 8/1994 | Tam | G06T 11/006 345/419 |
| 5,654,820 | A * | 8/1997 | Lu | G06T 11/006 342/179 |
| 5,881,122 | A * | 3/1999 | Crawford | A61B 6/027 378/4 |
| 5,909,477 | A * | 6/1999 | Crawford | A61B 6/032 378/4 |
| 6,002,738 | A * | 12/1999 | Cabral | G06T 11/006 378/15 |
| 6,115,446 | A * | 9/2000 | Pan | G06T 11/006 378/136 |
| 10,551,609 | B2 * | 2/2020 | Ripoll Lorenzo | G06T 15/00 |
| 2004/0076319 | A1 * | 4/2004 | Fauver | G01N 21/4795 382/133 |
| 2004/0086074 | A1 * | 5/2004 | Taguchi | G06T 11/005 378/4 |
| 2004/0240604 | A1 * | 12/2004 | Wang | A61B 6/027 378/19 |
| 2004/0258194 | A1 * | 12/2004 | Chen | G06T 11/006 378/4 |
| 2006/0232608 | A1 | 10/2006 | Riaz | |
| 2007/0153971 | A1 * | 7/2007 | Wang | A61B 6/503 378/8 |
| 2008/0056549 | A1 * | 3/2008 | Hamill | G06T 11/005 382/131 |
| 2008/0130974 | A1 | 6/2008 | Xu et al. | |
| 2008/0310698 | A1 * | 12/2008 | Boeing | G16H 40/63 382/131 |
| 2010/0189376 | A1 * | 7/2010 | Bertram | G06T 5/003 382/274 |
| 2011/0266453 | A1 * | 11/2011 | Tischenko | G06T 11/008 250/393 |
| 2012/0308100 | A1 * | 12/2012 | Pack | G06T 11/006 382/131 |
| 2012/0308102 | A1 * | 12/2012 | Pack | G06T 11/006 382/131 |
| 2014/0254905 | A1 * | 9/2014 | Pack | A61B 6/5205 382/131 |
| 2016/0239971 | A1 * | 8/2016 | Yu | H04N 5/32 |
| 2017/0221230 | A1 * | 8/2017 | Allinson | G06T 7/0012 |
| 2018/0286087 | A1 * | 10/2018 | Ray | G06T 11/006 |
| 2019/0156523 | A1 * | 5/2019 | Wang | G06T 7/0012 |
| 2019/0192101 | A1 * | 6/2019 | Manhart | A61B 6/507 |
| 2019/0206096 | A1 * | 7/2019 | Fu | G06T 11/005 |

FOREIGN PATENT DOCUMENTS

| | | |
|---|---|---|
| JP | 2008-526283 A | 7/2008 |
| JP | 2016-49455 A | 4/2016 |
| WO | 2013/105583 A1 | 7/2013 |
| WO | 2014/021349 A1 | 2/2014 |
| WO | 2014/185078 A1 | 11/2014 |
| WO | 2017/082785 A1 | 5/2017 |

OTHER PUBLICATIONS

Deans, "The Radon Transform and Some of Its Applications," John Wiley & Sons, 1983, 121 pages.

Kak, et al., "Principles of Computerized Tomographic Imaging," IEEE Press, 1988, 73 pages.

Kawamura et al., "Optical Computed Tomography for Polymer Gel Dosimetry," Japanese Journal of Medical Physics., 2017, vol. 37 (2), pp. 111-116 (with English Abstract).

Siddon, "Fast calculation of the exact radiological path for a three-dimensional CT array," Medical Physics, 1985, vol. 12 (2), pp. 252-255.

Sunnegårdh, et al., "A New Anti-Aliased Projection Operator for Iterative CT Reconstruction," 9th International Meeting of Fully Three-Dimensional Image Reconstruction in Radiology and Nuclear Medicine, 2009, pp. 125-127.

* cited by examiner

N=2×Odd

N=2×Even

N=2×Even

ACQUISITION METHOD, ACQUISITION DEVICE, AND CONTROL PROGRAM FOR TOMOGRAPHIC IMAGE DATA BY MEANS OF ANGULAR OFFSET

BACKGROUND

Technical Field

The present disclosure relates to a method for acquiring tomographic image data, an acquisition apparatus, and a control program by an angle offset. More particularly, the present disclosure relates to a method of acquiring tomographic image data, an acquisition apparatus, and a control program that incorporate an efficient algebraic method of discrete inverse Radon transform based on an angle offset.

Description of the Related Art

Tomography, or a tomographic imaging method using waves or particles having transmission nature such as X-rays, gamma rays, light waves, or waves or particles exhibiting any sort of permeability or transmission ability such as a seismic wave or other has been put into practical use. Typical examples include an X-ray CT scanner used in medical and industrial applications, SPECT (Single Photon Emission Computed Tomography), and Optical Tomography. In recent years, an optical CT device using visible light has been developed, and an imaging method using a gel dosimeter as an object is studied after its irradiation by radiation in order to verify three-dimensional distribution of radiation dose before performing radiation therapy of cancer. Mathematical principle assuring the tomographic image of the object by these imaging methods is Radon transform. In this context, the processing for capturing the attenuation rate of each part inside the object as imaging information from outside is described by Radon transform, and the processing for reconstructing the tomographic information of the object from the captured information is described by an inverse Radon transform. That is, the operation for detecting the flow of the wave or particles attenuated by the object at each position by changing the irradiation direction or the detection direction corresponds to the Radon transform. In contrast, an operation for reconstructing an image by estimating the attenuation rate of each part inside the object from the intensity information of each direction and each position of the detection corresponds to the inverse Radon transform. The Radon- or inverse Radon transform for continuous coordinates and continuous directions for real images is carried out using sampling points on coordinates or orientations for handling a finite number of pixels. The inverse Radon transform (discrete inverse Radon transform) for image reconstruction under sampled coordinates and orientations is reduced into solving multiple simultaneous linear equations or matrix operations. These mathematical aspects are described in standard textbooks (e.g., Non-Patent Documents 1 and 2).

Iterative reconstruction (IR), which is accompanied by iterative approximation to reduce noise and artifacts, has also attracted attention. The iteration process is repeated, for example, 100 times or more to obtain the solution. Such a technique for obtaining a reconstructed image by deriving an approximate solution of multiple simultaneous linear equations by relying on an algebraic method is called an ART (Algebraic Reconstruction Technique). The ARTs include techniques that are referred to as, for example, a Maximum Likelihood-Expectation Maximization (ML-EM) method, an Additive-Simultaneous Iterative Reconstruction Techniques (ASIRT), and a Multiplicative-Simultaneous Iterative Reconstruction Techniques (MSIRT). In conventional ARTs, a calculation scale becomes huge and a large amount of computational resources are required. In addition, repeated iterations often do not approach the solution corresponding to the true image and are captured by the local solution. On the other hand, approximation calculation efficiency in computing has been improved without resorting algebraic methods while utilizing realistic calculation resources. Such examples include FBP (Filtered Back Projection) (for example, Patent Document 1). Since the scale of calculation is small in the FBP, it is currently most frequently used with X-ray CT scanners.

In the course of the progress of the tomographic imaging methods from the beginning to date, there has been a continuing demand for increasing the number of imaging pixels, and therefore the possibility of the FBP has been intensively studied. The FBP is, however, generally disadvantageous in the quality of reconstructed images in which various artifacts are readily developed compared to IR. Nowadays, the ARTs, which are intrinsically advantageous in the quality of a reconstructed image, have been attracted much attention again based on continuing development of computational powers (see, for example, Patent Document 2).

CITATION LIST

Patent Documents

Patent Document 1: WO2014/021349
Patent Document 2: WO2013/105583

Non-Patent Documents

Non-Patent Document 1: Aviash, C Kak and Molcolm, Slaney, "Principles of Computerized Tomographic Imaging," IEEE Press (1988)
Non-Patent Document 2: Stanley R. Deans, "The Radon Transform and Some of Its Applications," Krieger Publications (1983)
Non-Patent Document 3: Robert L Siddon, "Fast calculation of the exact radiological path for a three-dimensional CT array," Medical Physics, vol. 12, no. 2, pages 252-255 (1985)
Non-Patent Document 4: Sunnegardh, J. and Danielsson, P.-E. "A New Anti-Aliased Projection Operator for Iterative CT Reconstruction," 9th International Meeting of Fully Three-Dimensional Image Reconstruction in Radiology and Nuclear Medicine, pages 125-127 (2009)

BRIEF SUMMARY

Technical Problem

There is continuing need for quality of reconstructed images in addition to the quest for increasing the number of pixels for improving the definition of images. Even when a conventional ART is adopted in a situation in which the number of imaging pixels is increased, the number of dimensions of the simultaneous linear equation to be solved, or variables to be determined, is increased, which requires a huge scale of calculation resources and takes a long time for processing. Therefore, in order to seek practicability in image data acquisition processing by way of the conventional ART, all we can do is to wait for the improvement of the calculation capability. In particular, it is not practical to obtain a large number of tomographic images, for example, to obtain a three-dimensional volume image while relying upon the conventional ARTs, which requires re-execution for each imaging for the iterative calculation accompanying iterative approximation.

The present disclosure addresses at least some of the problems mentioned above. The present disclosure provides a high degree of practicality for high quality tomographic imaging methodology by employing a new sampling technique that is supported by an algebraic exact solution for the discrete inverse Radon transform, which is responsible for image reconstruction.

Solution to Problem

The inventors realized that the problem with conventional ARTs is due to their discretization procedures, such as sampling. Conventional ARTs contain a large number of overlapping equations in a multidimensional system of linear equations, and the number of available equations is practically insufficient in comparison with the number of variables to be determined. As a result an iterative approximation has been required and the effort has been directed to the improvement of computation performance of processors. To address the above problem, the inventor has completed a new solution by re-examining it from the discretization method in which the unconventional sampling is combined with appropriate processing.

That is, in certain aspects of the present disclosure provided is A method for acquiring image data comprising: a step of disposing an object in a detection range of a detection device having N detection elements (N is a positive integer) arranged in at least one row; a step of detection in which detection operations for obtaining an intensity value for each of the detection elements by receiving transmitted waves or particles by each of the detection elements are performed, where the waves or particles are detectable by the detection device, in each of relative detection directions for the waves or particles viewed from the object, while irradiation of the waves or particles toward the detection device by an irradiation device is performed, or while the waves or particles generated without the irradiation device are transmitted through each part of the object; a vectorization step for obtaining a first vector with N×N elements from a detection signal by the detection device in the detection operations, wherein the elements of the first vector corresponding to those obtained by vectorizing a sinogram with N rows and N columns, each row and each column of which are associated with each detection direction and each detection element, respectively; a discrete inverse Radon transform step of operating a discrete inverse Radon transform matrix to the first vector to obtain a second vector having N×N elements; and an image data generation step, by de-vectorizing the second vector, for obtaining image data for a two-dimensional tomographic image of N pixels×N pixels having a pixel arrangement in which each pixel is addressed by two-dimensional coordinates where two coordinate axes are defined for the object with a common pitch in vertical and horizontal axes, wherein said each detection direction in the step of detection is an angle sampling direction corresponding to each angle increment equally dividing an angle scan range into N divisions for reconstructing the two-dimensional tomographic image, wherein one of two directions adjacent to each of two boundaries is offset from one of the coordinate axes and the offset angle is greater than 0° and less than 90° or greater than −90° and less than 0°.

The present disclosure can also be implemented in an aspect of a tomographic image data acquisition device. Similarly, the present disclosure can be implemented in an aspect of a control program for a tomographic image data acquisition device.

Furthermore, in any aspect of the present disclosure, it is preferred that either of the two boundary directions defining the angle scan range is offset from the coordinate axis by an offset angle of more than 0 degrees but less than 90 degrees. The offset angle is set to an angle, for example, 45 degrees, but a different value may be adopted depending on the value of the integer N. In addition, a plurality of offset angles may be suitable for the same integer N. Unless otherwise noted below, the number of detection elements N refers to the number of effective detection elements included in the detection device. In the present application, including these, we may use terminology that follows the conventions of the art to which the disclosure belongs unless it renders the description unclear. Waves may include any sort of wave that can be conceived of as attenuated through propagation, such as electromagnetic waves, sound waves, and may include light waves (infrared, visible, and ultraviolet) and oscillations (e.g., seismic waves). Particles include any sort of particles that can be conceived of as attenuated through propagation in a stream of particle rays, including neutron rays and other radiation. Anything that may have properties both of wave and particle in a quantum mechanical sense, such as electrons and photons, is also included in either or both of the waves or particles. Similarly, anything that is regarded as waves or particles in a classical mechanics point of view is also included in one or both of the waves or particles. These waves or particles can be used in the practice of the present disclosure, even they are generated by a device or an emitting device, that is an artificial source of their emission, or may be generated from natural sources, for example, cosmic rays, or generated due to a property of the object, for example, radiation emitted from various parts of the interior of the object, which are referred to as "waves or particles that are not generated by the emitting device" in this application.

Advantageous Effects of Disclosure

In certain aspects of the present disclosure, a high-definition and high-quality reconstructed image can be acquired at a high speed while using a relatively small computational resources.

BRIEF DESCRIPTION OF THE SEVERAL VIEWS OF THE DRAWINGS

FIG. 5A, FIG. 5B, and FIG. 5C indicate calculation examples of calculated ranks of the system matrices with respect to the offset angle in an embodiment of the present disclosure, wherein FIGS. 5A to 5C are for resolutions N of 4, 6, and 8, respectively.

FIG. 6A, FIG. 6B, and FIG. 6C indicate calculation examples ranks of system matrices for the offset angle in an embodiment of the present disclosure, wherein FIGS. 6A-6C are for resolutions N of 10, 12, and 14, respectively.

DETAILED DESCRIPTION

Figure 1A:
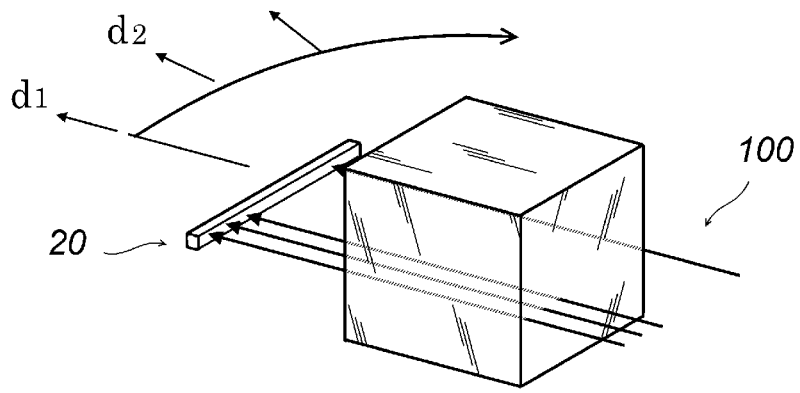
FIG. 1A and FIG. 1B indicate a perspective view illustrating the relationship between the object to be imaged and the detection device in one example of a tomographic imaging device in which an image is acquired in an embodiment of the present disclosure (FIG. 1A), and a schematic view illustrating a general configuration including a planar arrangement in a cut plane of the object to be imaged (FIG. 1B).

The embodiments of tomographic imaging according to the present disclosure will be described herein with reference to the accompanying drawings. For all drawings, the common reference numerals are given to common part or element unless otherwise noted. In addition, each element in the drawing should be understood as not being drawn to scale.

1. The Principle

Figure 1B:
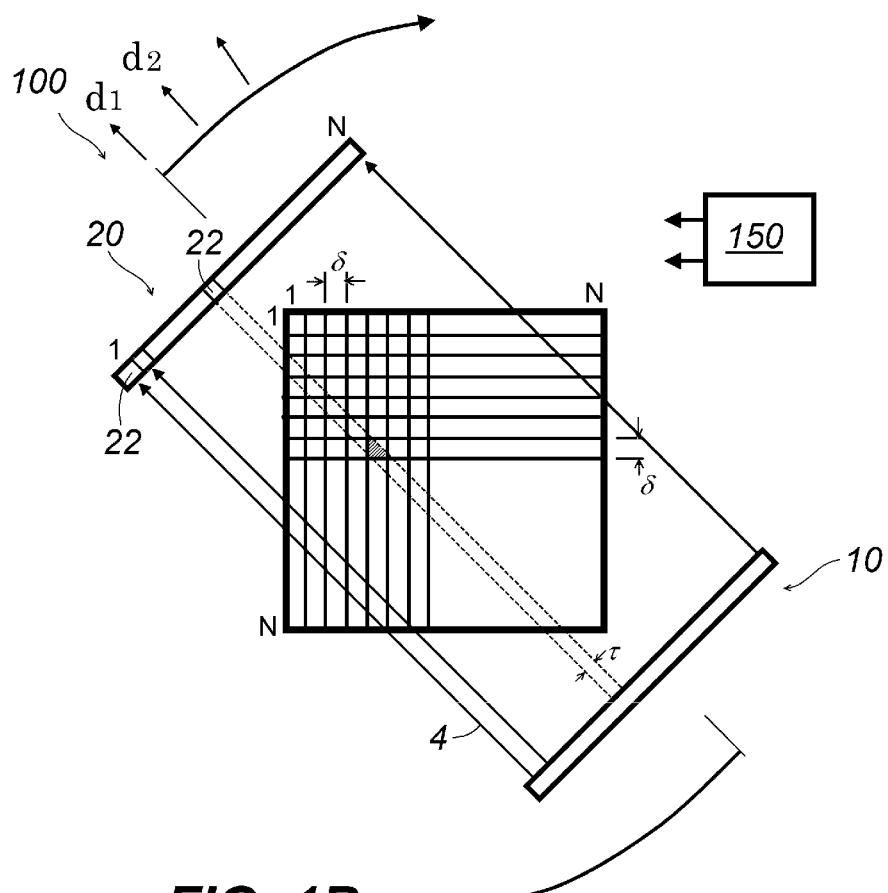

The illustrative geometric configuration in the present embodiment will be described. FIG. 1A and FIG. 1B are schematic diagrams for illustrating a schematic configuration including a planar arrangement at a cutting plane of the object for which an image is captured, in one example tomographic imaging device 100 where an image of the present embodiment is acquired. A group of pixels having N pixels×N pixels in a plane in the space that is fixed to the object (not shown in FIG. 1A and FIG. 1B) is defined. Typically, the integer N is made to coincide with the number of detection elements 22 of the detection device 20. For that reason, we may refer to the integer N as the resolution N in particular in this embodiment. A beam of waves or particles 4 is contained in the plane thereof and is emitted from the emitting device 10. The detection device 20 and the emission device 10 are able to be rotated with respect to the object while their relative configuration remains fixed. For the operation and computational processing of a device that includes such a control, the tomographic imaging device 100 is equipped with a control device 150, which may be a computer device. That rotation is relative to the above-mentioned group of pixels and the objects stationary therein. Accordingly, it is not necessarily limited that the detection device 20 and the emission device 10 alone are rotated, but the detection device 20 and the emission device 10 may be fixed to the installation floor surface (not shown) and the object may be rotated together with a group of pixels.

The operation of irradiating a beam of waves or particles 4 by the emission device 10 and detecting the beam 4 across the object by the detection device 20 will be sampled at intervals dividing the scan range of the detection direction θ by the number of pixels N for the detection direction. For a beam 4 parallel as shown in FIG. 1B, the angle scan range covered by the detection direction θ is conventionally set to, for example, from 0 to 180°, and the detection signal from the detection device 20 is sampled in intervals of (180/N)°. In such a case, detection directions that are in close proximity to the boundaries of the angle scan range are made parallel or perpendicular to the coordinate axes for specifying pixels of the image to be reconstructed, for example. In the case where the detection direction is parallel or perpendicular to either of the coordinate axes, then there is no offset in the angle. Typical scanning operations for the detection directions $d_1$ to $d_N$ of the tomographic imaging device 100, including this embodiment, are sampled by electrically controlling the timing of obtaining the values of the detection device 20 while rotating at a constant speed that increases or decreases the detection direction θ at a constant rate. However, the present embodiment is not limited to this type of operation.

Figure 2:
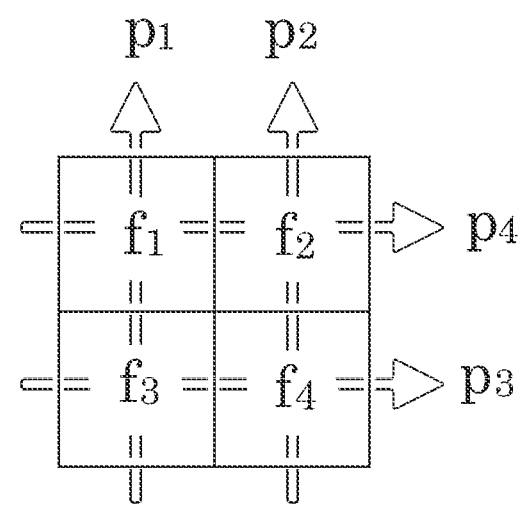
FIG. 2 is an explanatory diagram illustrating the principle of an algebraic method of a conventional discrete inverse Radon transform.

FIG. 2 is an illustration of the principle of the conventional algebraic method of discrete inverse Radon transform. The schematic illustrates the primitive nature of the process of irradiating a wave or particle and reconstructing a tomographic image using the intensity data after transmission. The illustrated square region arranged in 2 vertical×2 horizontal squares, each of which is meant to be a pixel in a tomographic image for a resolution of N=2, may have four values $f_1$ to $f_4$. The values represent the degree of beam attenuation by the object at each pixel location and are to be determined. White arrows drawn through the multiple pixels and oriented 180°/N, i.e., 90° for a resolution of N=2, correspond to the irradiation of the beam of waves or particles and the positions of the detector elements. The values pointed to by the arrows refer to the numerical values obtained when the detector elements of the detection device are located ahead of the arrows (e.g., the degree of attenuation), and here the sum of the values for the pixels through which the arrows pass is indicated by numerical values. That is, the arrows represent a beam of waves or particles, and the pixels through which the arrows pass and the directions of the arrows indicate the irradiation and detection (hereafter referred to only as "irradiation"). The total values at the tip of the arrows correspond to the attenuation component detected at each of the detection elements of the detection device when there are detection elements of the detection device at the tip of the arrows. The determination of the four values from $f_1$ to $f_4$ only according to the values indicated by the arrows, i.e., the values obtained from the detection device, corresponds to the process of reconstructing the tomographic image by performing a discrete inverse Radon transform based on the values indicated by the detection elements of the detection device.

In the example shown in FIG. 2, what are connected by each of the arrows in $f_1$ to $f_4$ provide linear sums, which can be rewritten into the following simultaneous equations.

Math 1

$$p_1=f_1+f_3, \; p_2=f_2+f_4,$$
$$p_3=f_3+f_4, \; p_4=f_1+f_2, \quad (1)$$

Here, to illustrate the case of x-ray CT, $p_1$ to $p_4$ are the values measured at each pixel and in each detection direction of the x-ray in FIG. 2, and $f_1$ to $f_4$ are the x-ray absorption coefficients. This system of simultaneous equations does not allow us to determine a unique value. Instead, even if we substitute the values as Math 2

$$f_1 \rightarrow f'_1 = f_1+A, \; f_2 \rightarrow f'_2 = f_2-A,$$
$$f_3 \rightarrow f'_3 = f_3-A, \; f_4 \rightarrow f'_4 = f_4+A, \quad (2)$$

Formula (1) remains unchanged even when the $f_1$-$f_4$ are substituted with any shifted values. That is, while Formula (1) has four dimensions, i.e., variables to be determined are four, the number of equations that can be derived by the detection in the system of simultaneous equations indicated by the arrows is substantially three. In this case, all four values of $f_1$ to $f_4$ are indeterminate and cannot be determined.

Organizing this relationship by another mathematical relationship, Formula (1) above is expressed in a matrix form more generally as Math 3

$$\begin{pmatrix} p_1 \\ p_2 \\ p_3 \\ p_4 \end{pmatrix} = \begin{pmatrix} 1 & 0 & 1 & 0 \\ 0 & 1 & 0 & 1 \\ 0 & 0 & 1 & 1 \\ 1 & 1 & 0 & 0 \end{pmatrix} \begin{pmatrix} f_1 \\ f_2 \\ f_3 \\ f_4 \end{pmatrix} \Leftrightarrow p_n = \sum_m w_{nm} f_m \quad (3)$$

where, $w_{nm}$ are elements of the matrix W, which is a square matrix of $N^2$ rows and $N^2$ columns called the "system matrix". In general, the that a matrix W can have an inverse matrix $W^{-1}$ is said that W is regular and can be judged by various mathematical methods. And one of the typical methods is the determination by rank values. That is, the fact that the matrix W is regular is equivalent to the fact that the rank of the square matrix W in row N2 and column N2 (rank($w_{nm}$)) reaches N×N. If the matrix W is regular, we can uniquely solve the simultaneous equations corresponding to Formula (1). In the matrix in Formula (3) above, the rank is calculated to be rank ($w_{nm}$)<4, which does not reach the value necessary for it to be regular, corresponding to N=2.

Figure 3A:
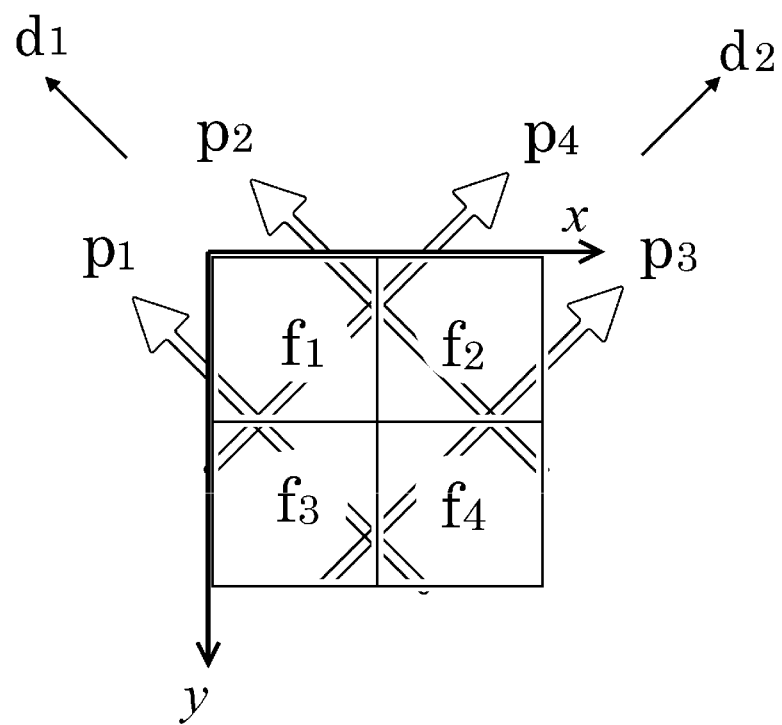
FIG. 3A and FIG. 3B indicate a schematic diagram illustrating the principle of the algebraic method of the discrete inverse Radon transform of an embodiment of the present disclosure, wherein FIG. 3A indicates the relationship between the pixels and the detection direction of detection for a resolution N of 2, and FIG. 3B indicates the relationship between the coordinate axes and the detection direction of the image for a general resolution N.
Figure 3B:
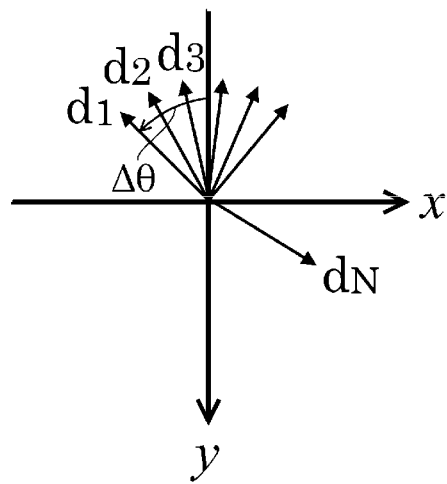

FIG. 3A and FIG. 3B provide an illustration of the principle of the algebraic method of the discrete inverse Radon transform of the present embodiment. FIG. 3A indicates the relationship between the pixels and the detection direction for a resolution N of 2, and FIG. 3B indicates the relationship between the coordinate axes and the detection direction of the image for a general resolution of N. The present embodiment, most straightforwardly, performs detection operations by offsetting and shifting the detection direction from FIG. 2 entirely, as shown in FIG. 3A. In FIG. 3A, the detection directions $d_1$ and $d_2$ are representative of the detection directions of a plurality of pixels indicated by the white arrows, and an offset angle of −45° is used.

In the example of this embodiment in FIG. 3A, the equation corresponding to equation (1) above is Math 4

$$p_1=f_1+f_3+f_4, \; p_2=f_1+f_2+f_4$$
$$p_3+f_2+f_3+f_4, \; p_4=f_1+f_2+f_3, \quad (4)$$

and if we find the rank in the same way, then rank($w_{nm}$)=4, reaching N×N. In other words, in the present embodiment, $f_1$ to $f_4$ can be uniquely determined. In fact, Formula (4) is simplified as Math 5

$$\begin{pmatrix} p_1 \\ p_2 \\ p_3 \\ p_4 \end{pmatrix} = \begin{pmatrix} 1 & 0 & 1 & 1 \\ 1 & 1 & 0 & 1 \\ 0 & 1 & 1 & 1 \\ 1 & 1 & 1 & 0 \end{pmatrix} \begin{pmatrix} f_1 \\ f_2 \\ f_3 \\ f_4 \end{pmatrix} \Leftrightarrow p_n = \sum_m w_{nm} f_m \quad (5)$$

and the inverse matrix $W^{-1}$ (also described as $\{w_{nm}^{-1}\}$) is organized as Math 6

$$w_{nm}^{-1} = \frac{1}{3} \begin{pmatrix} 1 & 1 & -2 & 1 \\ -2 & 1 & 1 & 1 \\ 1 & -2 & 1 & 1 \\ 1 & 1 & 1 & -2 \end{pmatrix} \quad (6)$$

That is to say, it is possible to uniquely determine $f_1$ to $f_4$ only by the algebraically rigorous method of letting this inverse matrix operate on the measured values $p_1$ to $p_4$. The inventors discovered a phenomenon that can determine a system matrix having an inverse matrix simply by shifting the direction of detection, and named it Initial Phase Effect (IPE). The IPE is an extremely practical technique because it means that in the actual measurement process, the detection operation can be performed in a direction that is offset from the coordinate axis that specifies the pixels of the two-dimensional reconstructed image by shifting the timing of sampling of the angle and so on.

Next, we checked whether IPE is valid for a more general resolution N. FIG. 3B illustrates the relationship between the coordinate axis and detection directions of the image for general resolution N. For ease of understanding at resolution N, we focus only on the directions (coordinate axes and detection directions). For general resolution N, the values to be determined, such as $f_1$ to $f_4$ in FIG. 3A, are expressed as $f_1$ to $f_{N \times N}$ (not shown). These values $f_1$ to $f_{N \times N}$ correspond to each pixel of an N×N pixels two-dimensional tomographic image, for example, specified in two-dimensional orthogonal coordinates. Since the image is defined to be stationary, for example, with respect to an object not shown in the figure, the image is spread out along the x and y axes, which are the coordinate axes, and the pixels can be identified by the values of the coordinate axes. In the present embodiment, the detection directions are also made in the direction of the detection direction $d_1$ to $d_N$, where the detection range is divided into N divisions (FIG. 3B). In the present embodiment, neither of the detection directions $d_1$ to $d_N$ are parallel or perpendicular to either the x-axis or the y-axis. The offset angle described above is more generally determined between the two detection directions that are nearest neighbors (in angle) to the two boundary directions that define the detection scan range and either coordinate axis. Referring back to FIG. 3A, the offset angle $\Delta\theta$ can be in a range of 180° from the negative direction of the x-axis to the positive direction of the x-axis in a clockwise direction, so that it is set at −45° between the detection direction $d_1$, which is the nearest neighbor to the negative direction of the x-axis, and the negative direction of the y-axis, which is the coordinate axis (the upper direction on the paper). It should be noted that, although the detection directions are included within the range of directions of the detection scan range, the offset angle is determined with respect to the detection direction and the coordinate axis of the image, rather than the detection scan range. This is related to the fact that there is some degree of allowances for the way the detection scan range is taken. For example, even with the fixed detection directions $d_1$ and $d_2$ in FIG. 3A, the detection scan range can be considered as a 180° range from the negative direction of the x-axis to the positive direction of the x-axis clockwise, which is the range from 9 o'clock to 3 o'clock in the direction of the clock dial with 12 o'clock above the paper in FIG. 3A; in contrast, the detection scan range may be considered as a 180° range from the direction of the bisectors at 9 and 12 o'clock (10.5 o'clock or 10:30) to the direction of the bisectors at 3 and 6 o'clock (4.5 o'clock or 4:30). In general, the detection directions $d_1$ to $d_N$ should be the sampling direction corresponding to each of the angle intervals that equally divide the detection scan range into N segments (N equal divisions). As shown in FIG. 3B, in the case of a general resolution N, a number of detection directions $d_1$ to $d_N$ are set in accordance with the number of detection elements N. In the present embodiment, either of the detection directions $d_1$ to $d_N$ is set so that none of the detection directions $d_1$ to $d_N$ are parallel or perpendicular to either of the x-axis or the y-axis. In this case, the offset angle $\Delta\theta$ is determined with respect to either the x-axis or the y-axis with respect to the detection direction $d_1$ or the detection direction $d_N$. In the present embodiment, as long as the offset angle $\Delta\theta$ is relatively defined between the coordinate axis for the image and the detection directions, the coordinate axis for the image and the detection directions themselves may be defined according to various conveniences. For example, if a coordinate axis for the image coincides with a coordinate axis of the device, the offset angle $\Delta\theta$ can be achieved by adjusting the detection directions. Conversely, if a detection direction is coincident with a coordinate axis of the device, the offset angle $\Delta\theta$ can be achieved by rotating the coordinate axes for the image.

Figure 4:
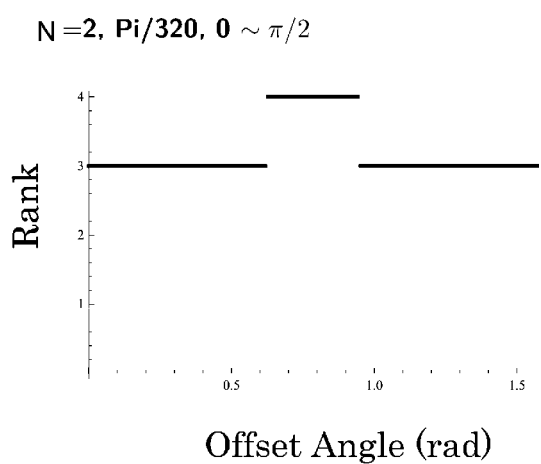
FIG. 4 indicates calculation examples of the ranks for system matrices with respect to the offset angle in an embodiment of the present disclosure, in the case of a resolution N of 2 shown in FIG. 3.
Figure 5A:
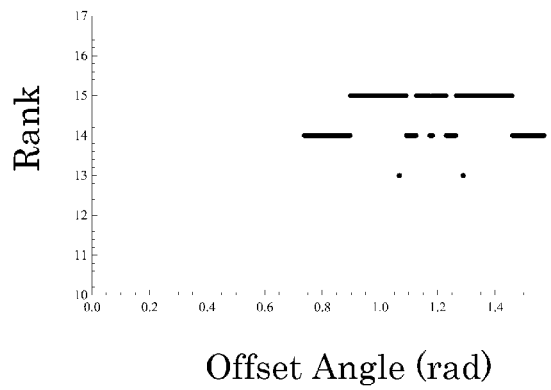
Figure 5B:
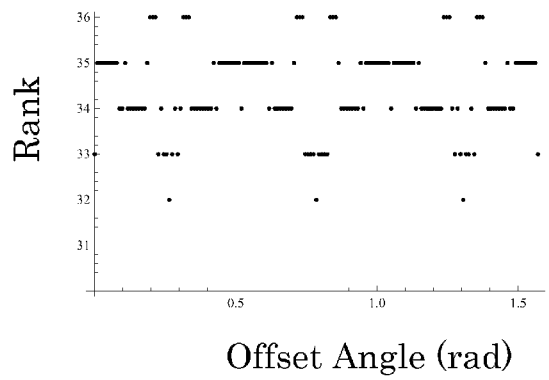
Figure 5C:
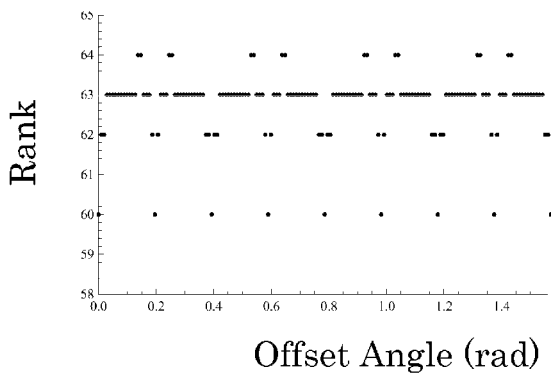
Figure 6A:
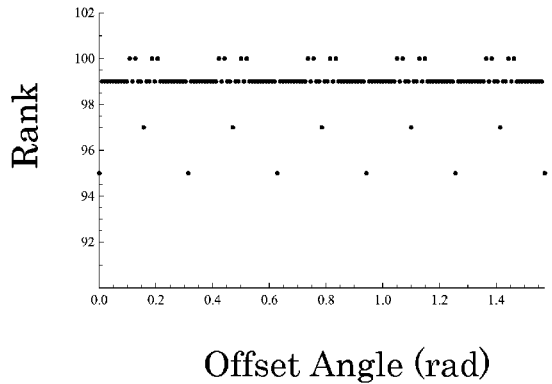
Figure 6B:
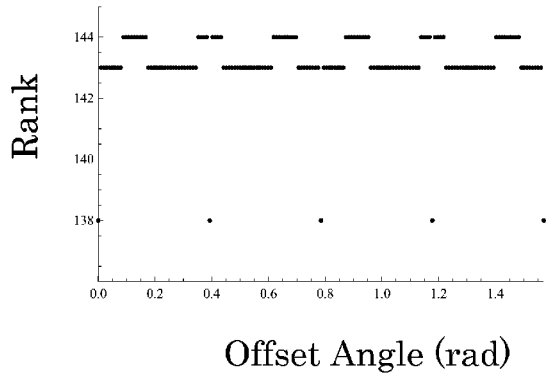
Figure 6C:
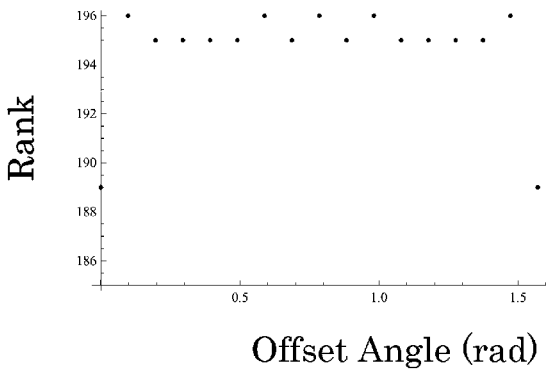

The effectiveness of IPE in the generalized resolution of N was confirmed by numerical calculations. FIG. 4 shows calculation examples of the ranks for system matrices with respect to the offset angles at a resolution of N=2. The horizontal axis denotes the offset angle in radians, and the vertical axis denotes the rank for each offset angle value. The calculations were performed using the Mathematica (Wolfram Research, Inc., Champaign, Ill.) mathematical processing software, and the offset angle was varied in steps $\pi/320$ (rad) over a range of 0 to $\pi/2$ (rad) (0 to 90°). These conditions are clearly shown above in the figure. Corresponding to FIG. 2 is the position of the horizontal axis 0 or $\pi/2$ (approx. 1.57) (rad). Corresponding to FIG. 3A is the position of $\pi/4$ (rad). In this case, the system matrix W has an inverse matrix $W^{-1}$ as shown in Formulas (4)-(6), and the rank is 4 (i.e., N×N) at an offset angle $\pi/4$ (rad). This was confirmed numerically using the more general resolution N, and the results in FIGS. 5A-5C and FIGS. 6A-6C were obtained. FIGS. 5A-5C are those with a resolution N of 4, 6, and 8, and FIGS. 6A-6C are those with a resolution N of 10, 12, and 14, respectively. For FIG. 5A, the offset angle was calculated in intervals of $\pi/32000$ (rad), thus limiting the range of the calculated offset angle to $7.5\pi/32$ to $\pi/2$ (rad).

In addition to the results shown in the figure, the inventors have confirmed that the effectiveness of IPE, i.e., at each resolution N, is as follows:

For N=4, the ranks do not appear to be equal to N×N.

It was confirmed that at the following resolutions, ranks=N×N.

N=2, 6, 8, 10, 12, 14, 16, 18, 20, 22, 24, 26, 28, 30, 32, 34, 36, 38, 40, 42, 44, 46, 48, 64, 126, 128, 130.

That is, by introducing an offset angle, the condition of rank=N×N was achieved in many cases, and the decrease in the rank (rank drop) seen in the case of FIG. 2 was confirmed to be eliminated. Thus, the IPE was found to be effective at many practical resolutions N, through the introduction of an offset angle.

Figure 7A:
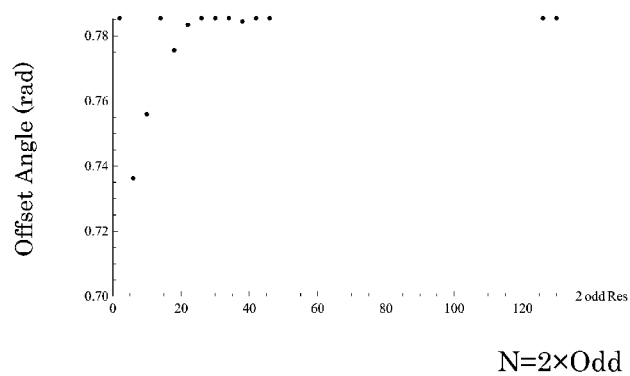
FIG. 7A, FIG. 7B, and FIG. 7C indicate graphs plotting example values of offset angles having ranks $N^2$ for each N in embodiments of the present disclosure, for resolutions N of integers that are twice of odd numbers (FIG. 7A), for resolutions N of integers that are twice of even numbers (FIG. 7B), and with fitting curves by an analytical function overlaid on each point in FIG. 7B (FIG. 7C).
Figure 7B:
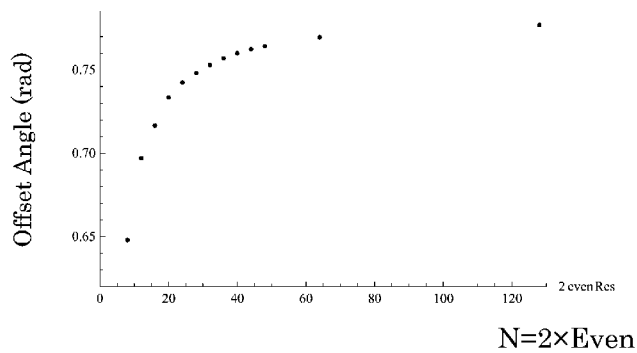
Figure 7C:
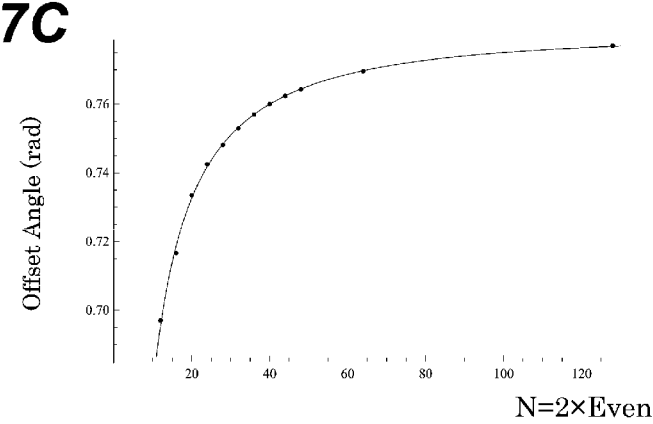

Based on the results confirmed by numerical calculations, the inventors paid attention to the regularity of the ranks that vary with the resolution N. Specifically, we examined that the rank drop was resolved in the vicinity of an offset angle of $\pi/4$ (rad) (45°). In the first place, the symmetry was relatively clear: when the offset angle was varied from 0 to $\pi/2$ (rad), the graphs in FIGS. 4-6C had a symmetrical relationship around $\pi/4$ (rad). We also noticed different trends between those with a resolution N of 2×odd and those with a resolution N of 2×even. That is, when N is 2×odd, one of the ranges of offset angles from which the ranks are recovered seems to appear relatively closer to $\pi/4$ (rad) than in the 2×even case. FIG. 7A, FIG. 7B, and FIG. 7C provide graphs that plot example values of offset angles with a rank of $N^2$ for each N, with the fitting curve by the analytical function overlaid on each point in the present embodiment, when the resolution is N for an integer that is twice of odd numbers (FIG. 7A), and when the resolution is N for an integer that is twice of even numbers (FIG. 7B), and with the fitting curve by the analytical function overlaid on each point in FIG. 7B (FIG. 7C).

At present, due to computational resource constraints, the maximum resolution N at which the effectiveness of the IPE that resolves the rank drop has been confirmed is N=130.

Table 1 provides the offset angles for the resolution N such that the offset angles with ranks=N×N are closest to $\pi/4$ (rad) when such offset angles are observed at multiple values or ranges while changing the offset angle from 0 to $\pi/4$ (rad).

TABLE 1

| N | Offset (rad) |
|---|---|
| 2 | $\pi/4$ |
| 4 | — |
| 6 | 0.736311 |
| 8 | 0.647953 |
| 10 | 0.755946 |
| 12 | 0.697041 |
| 14 | $\pi/4$ |
| 16 | 0.716676 |
| 18 | 0.775581 |
| 20 | 0.733493 |
| 22 | 0.783398 |
| 24 | 0.742493 |
| 26 | $\pi/4$ |

TABLE 1-continued

| N | Offset (rad) |
|---|---|
| 28 | 0.7481 |
| 30 | $\pi/4$ |
| 32 | 0.753 |
| 34 | $\pi/4$ |
| 36 | 0.757 |
| 38 | 0.784398 |
| 40 | 0.760 |
| 42 | $\pi/4$ |
| 44 | 0.7624 |
| 46 | $\pi/4$ |
| 48 | 0.7643 |
| 64 | 0.7696 |
| 126 | $\pi/4$ |
| 128 | 0.7770 |
| 130 | $\pi/4$ |

In order to predict the position where the effective offset angle of IPE emerges at a larger size resolution N, a formula that can explain the calculation results well in the calculated range as in FIG. 7C is used:

Math 7

$$\text{Offset Angle} = b - \frac{a}{X} e^{-kx} \text{(rad)} \quad (7)$$

$$a = 1.12867, b = 0.779526, k = 9.22543 \times 10^{-3}$$

$$x = N$$

The followings are obtained, for example:

Offset angle=0.779506 (rad)(44.662°) for N=512 Offset angle=0.779526 (rad)(44.663°) for N=1024

At present, the inventors have found the followings on the principle aspects of the effectiveness of IPE:

By adjusting the offset angle, the indeterminacy about the values $f_1$ to $f_{N \times N}$ can be resolved and the values $f_1$ to $f_{N \times N}$ can be determined uniquely.

On the other hand, there is an example (N=4) where the resolution N, which may not be able to uniquely determine the value $f_1$ to $f_{N \times N}$, is found.

According to the above principle aspects, the present embodiment, which adopts an appropriate offset angle, allows for exact reconstruction of images using the algebraic solution method.

2. Specific Configuration

Next, the specific configuration of the image reconstruction method of the present embodiment employing the above principle will be described. As shown in FIG. 1A and FIG. 1B, the beam 4 has a spread covering all the pixel ranges at the above coordinates, and the portion toward each detector element 22 has a certain width τ. The contribution of the pixel in the beam 4 to the detection element 22 is typically the overlap between the width τ of the beam 4 toward one of the detection elements 22 and each pixel (each in length and width δ). In FIG. 1A and FIG. 1B, this overlap is shown as a pattern, and the contribution of all the pixels of N×N pixels is determined by the detection direction $d_1$ to $d_N$ and by the detector 22. This contribution is held as numerical values in the system matrix W described above. Expressing Formula (3) explicitly starting from the system matrix W2, the discrete Radon transformation representing irradiation and image reconstruction is represented by the product of the following matrix.

$$X' = WX \quad (8)$$

Here, the system matrix W usually takes the sequence of sampling points about the space according to the total number of pixels in the row direction and the sequence of sampling points about the irradiation and detection according to the increments of the detection direction and the detection elements in the column direction. When applied to the settings such as the number of pixels in FIG. 1A and FIG. 1B, the system matrix W is a square matrix with N×N elements in both the row and column directions, and the total number of elements is $N^4$. This is because the pixels are N pixels×N pixels, the scan range in the detection direction θ is N samples, and the number of detection elements 22 is N elements. The value of N has been increasing with time in order to improve the image quality, and in a typical example, the value of N is assumed to be 1024, or about $10^3$, and the maximum value is about 2000 in the conventional one. Even in the case of this embodiment, the value of N is not limited to a particular value of N. When N is about $10^3$, the system matrix has a size of about $10^6$ in both directional columns, and the number of elements is about $10^{12}$.

The X in Formula (8) represents the attenuation image, which is the image representing the attenuation (including absorption and scattering) at each pixel position, expressed as a column vector, and is the $f_m$ in Formula (3). The actual attenuation image in space is the N×N pixels two-dimensional image shown in FIG. 1A and FIG. 1B, but for the computation with the system matrix W, X is vectorized so that the row direction is the total number of pixels N×N. The column vector X' on the left-hand side, obtained by the operation of the system matrix W on the attenuated image X in Formula (1), corresponds to an image called a sinogram. Corresponding to the fact that the column direction in the system matrix W is the sequence of sampling points and detection elements in each of the detection directions, the column vector X' also represents the detection intensity obtained for each sampling point and detection element in the detection direction. The sinogram is a two-dimensional reordering of the elements of the column vector X' on the axis of the detection element and the axis of the detection direction increments. As described above, Formula (8) represents the irradiation and detection.

The reconstruction of a tomographic image is a process of calculating the column vector X from the system matrix W and the column vector X' of the sinogram, and obtaining the attenuated image from the column vector X, assuming that Formula (8) has been realized. In other words, the reconstruction of the tomographic image is formally expressed by the following equation $$X = W^{-1} X' \quad (9)$$

where $W^{-1}$ is the inverse matrix of W. Formula (9) is a swapped left and right sides of Formula (8) by operating $W^{-1}$ on both sides. The relationship between Formulas (8) and (9) is a compatible relationship between Formulas (5) and (6). And in the present embodiment, by setting an appropriate offset angle, it is possible to make W, which is a square matrix, to have an inverse matrix $W^{-1}$ and be regular in most cases of N. In the present embodiment, a method is proposed to determine with sufficient certainty the system matrix W, which is a regular square matrix that can have an inverse matrix $W^{-1}$, so that the final Formula (9) holds, and a sufficiently practical and specific configuration for irradiating, detecting, and reconstructing tomographic images is also provided for this purpose. Although the description based on FIG. 1A and FIG. 1B described above is for irradiating a parallel beam, the present embodiment can be applied by a slight modification obvious to those skilled in the art to the case of employing an emission device 10 or a detection device 20 that utilizes a beam that is not parallel, such as a fan beam or a cone beam. The method of the present embodiment can also be applied in other settings such as the number of pixels in FIG. 1A and FIG. 1B. Formulas (8) and (9) can also be expressed by other forms that are mathematically equivalent. For example, for the system matrix W, unlike the one described above, we take the sequence of sampling points for the space according to the total number of pixels in the column direction and the sequence of sampling points for the irradiation and detection according to the ticks and detection elements in the detection direction in the row direction. And correspondingly, the X in Formula (8) can be expressed as a row vector according to the position of each pixel. In that case, the expressions corresponding to Formulas (8) and (9) are transpose operations applied to each side. This transpose operation swaps the rows and columns of the matrix and vectors, and has the representational effect of changing the order in which the matrices that are to be operated on the vectors are operated from the right rather than from the left. When vectors are described alternatively as "column or row vectors" and the sequence of elements of the corresponding matrix is described alternatively as "column direction or direction", the choice of these combinations shall be selected by combining them in the same order in their respective selective descriptions. Since this choice of expression does not affect the substance of the application, an explanation will be given based on the notation that X, etc., which is a vectorized version of the sinogram, is represented by column vectors, and matrices, such as system matrices, are operated from the left, unless otherwise noted in the application, as in Formula (8).

2.1 Process Flow

Figure 8:
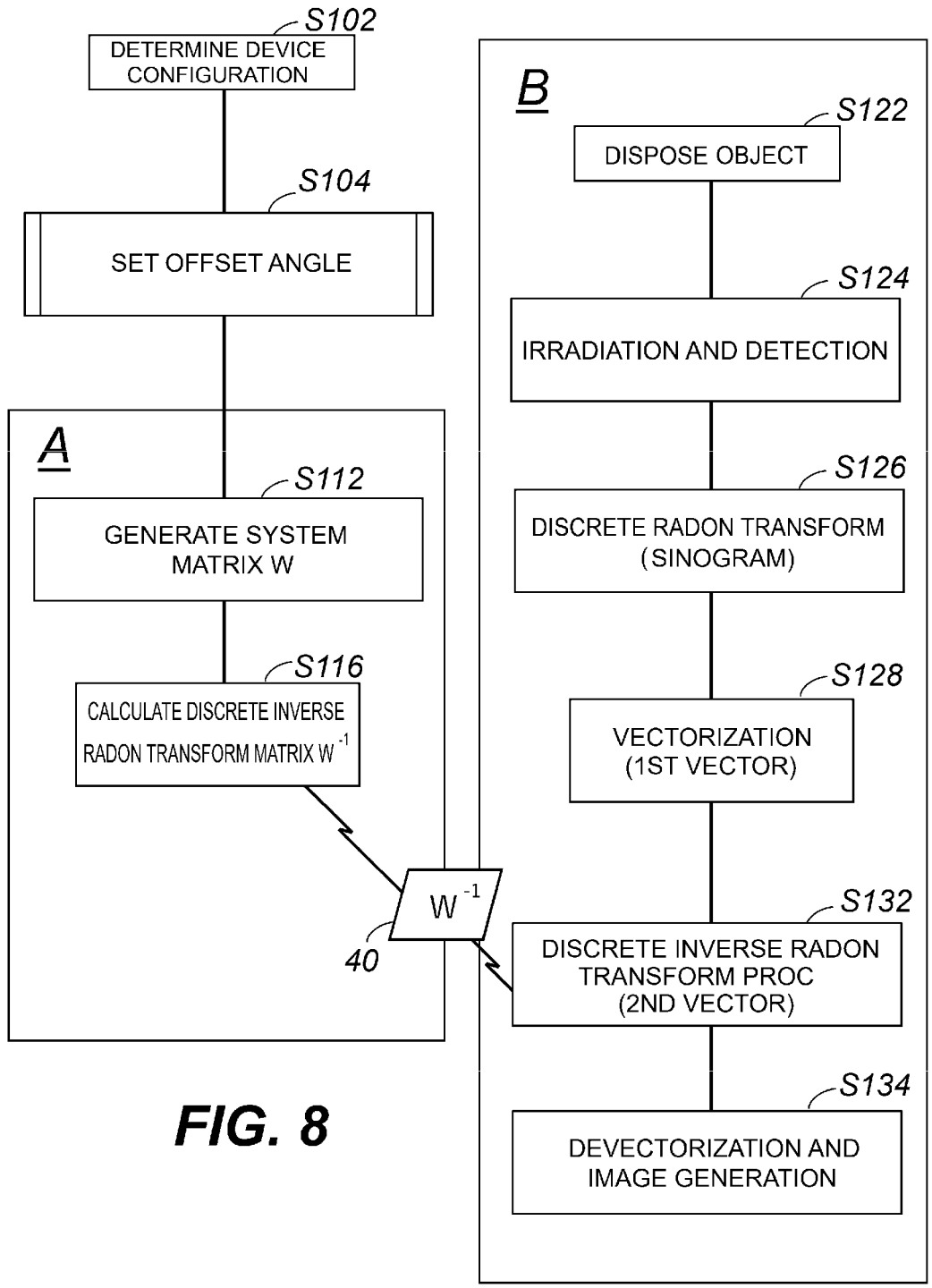
FIG. 8 illustrates a flowchart outlining a process performed in a control device of a tomographic imaging system of an embodiment of the present disclosure.
Figure 9:
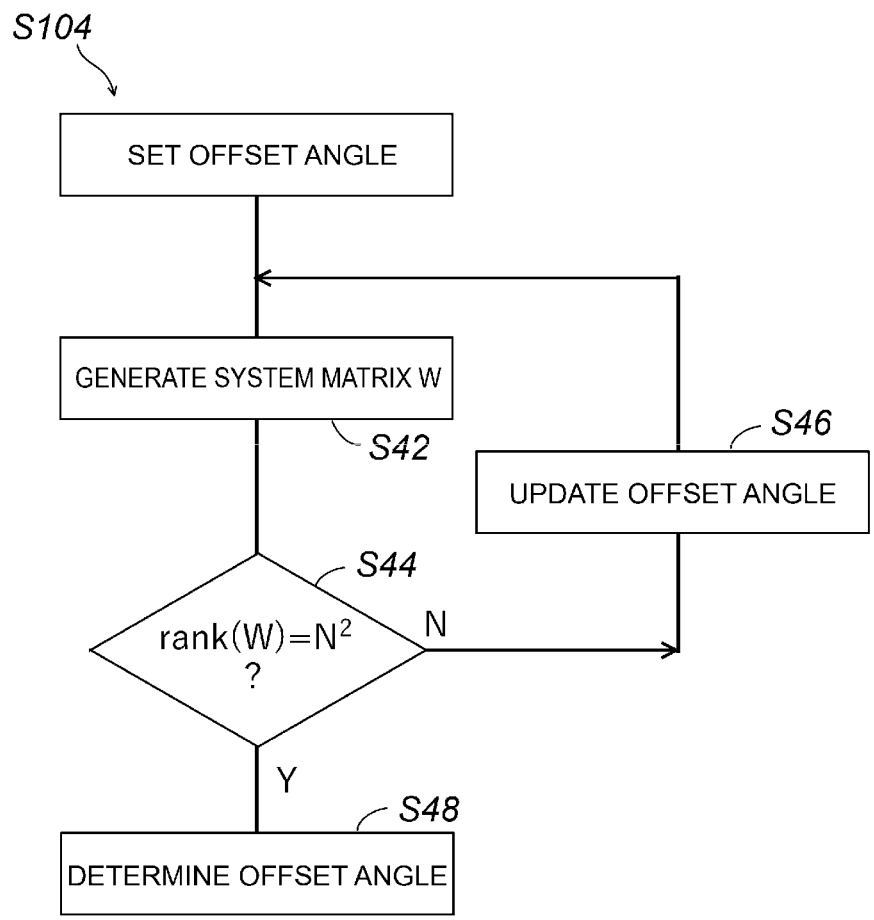
FIG. 9 illustrates a flowchart of an overview of the process of resetting an offset angle in a tomographic imaging system of an embodiment of the present disclosure.
Figure 10:
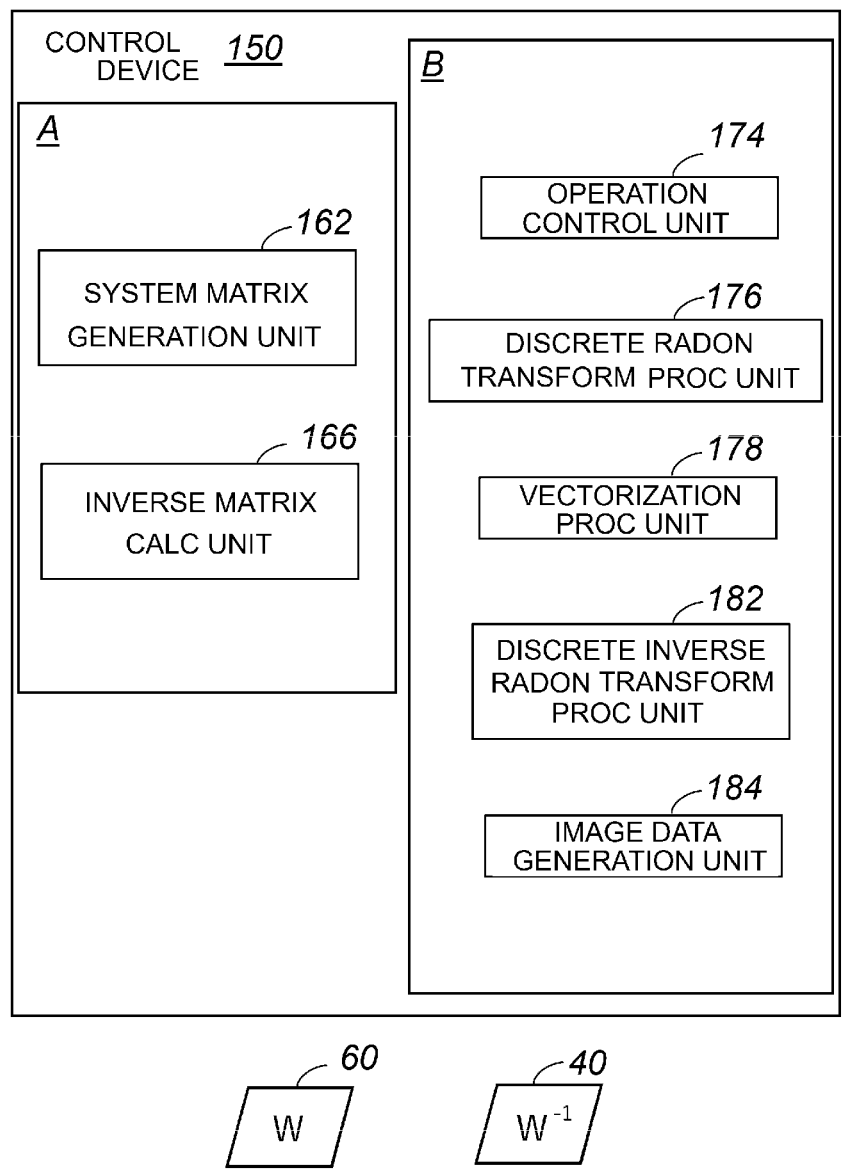
FIG. 10 illustrates a block diagram indicating specific functional units and specific data storage units of a control device when implementing the present embodiment by a tomographic imaging device.

The regular system matrix W is obtained in this embodiment because of the adoption of an appropriate offset angle. FIG. 8 is a flowchart outlining the process performed in the control device 150 of the tomographic imaging device 100 of the present embodiment, including these, and FIG. 9 is a flowchart outlining the process in the case of resetting the offset angle in the tomographic imaging device of the present embodiment. In addition, FIG. 10 is a block diagram showing specific functional units and specific data storage units of the control device 150 in the case of implementing this embodiment by the tomographic imaging device.

2.2 Outline of Process

In overview of the process performed in this embodiment, the configuration of the device is first determined (FIG. 8, S102). In the case of reconstructing an N pixels×N pixels (N is a positive integer) two-dimensional image in the later imaging, the number of detection elements 22 of the detection device 20 is also determined to be N. The detection directions $d_1$ to $d_N$ to be sampled are, in the conventional method, set in a range of 0 to 180 degrees in accordance with the axis of the image, where the angular scan range is, for example, in intervals of (180/N)°, e.g., with the positive or negative orientation of the x-axis or y-axis (FIG. 3A, 3B) as one boundary and the other boundary turned clockwise 180° from there, and so on. In contrast, the sampling of the detection direction of the present embodiment is set in a range of $\Delta\theta$ to $\Delta\theta+180°$ in intervals of (180/N)°, for example, offset from the negative direction of the y-axis (FIG. 3B) by an offset angle $\Delta\theta$ (e.g., an angle close to ±45°). The detection directions $d_1$ to $d_N$ are displaced by (180/N)° each, and the above offset angle is defined as the angle that the first or last detection direction $d_1$ or detection direction $d_N$ in the detection directions $d_1$ to $d_N$ make with either the x-axis or the y-axis. In this embodiment, the above offset angle is made to be more than −90° and less than 0° or more than 0° and less than 90°.

In order to obtain a tomographic image from the object 2 for obtaining an appropriate reconstructed image, the system matrix must be determined. To do this, the system matrix W is generated by the same process as the conventional system matrix, except the values are different due to the offset angle (S112). The system matrix W obtained here has only N×N elements in the column direction corresponding to the detection direction and the detection element respectively, and N×N elements in the row direction corresponding to the number of pixels in the tomographic image. The system matrix is stored in the system matrix storage unit 60 (FIG. 10). At this stage, if the offset angle $\Delta\theta$ is appropriate, the system matrix W is a regular matrix. From the system matrix W, its inverse matrix is calculated in the discrete inverse Radon transform matrix calculation step S116 and is stored in the discrete inverse Radon transform matrix storage unit 40. In this embodiment, the inverse matrix $W^{-1}$ is also called the discrete inverse Radon transform matrix. For the process of calculating the inverse matrix here, any method such as the remainder factor method or the sweeping method, for example, can be employed.

On the other hand, to obtain a tomographic image from the object, the object 2 is disposed between the emission device 10 and the detection device 20 having each detection element 22. For irradiation and detection using an offset angle, the detection is performed in the N directions while the beam 4 from the emission device 10 is irradiated (S124). In a typical implementation, this beam 4 continues to irradiate continuously and the orientation of the object 2, the emission device 10 and the detection device 20 (direction of detection) moves smoothly while the signal from the detection element 22 of the detection device 20 is electrically sampled. A typical example of irradiation and detection in the N directions is the repeated sampling of (180/N)° intervals with timing adjusted to have an offset angle $\Delta\theta$ with respect to the coordinate axis of the image. The resulting signal is organized into data that can generate a sinogram, provided that corrections and scale conversions are made for the physical characteristics of the instrument and the sequence order is organized, if necessary (S126). The organized data corresponds to the detection directions and detector positions that reflect the offset angle $\Delta\theta$. The process of obtaining this sinogram is the irradiation and detection process, which is a discrete Radon transform. From this sinogram, a column vector can be obtained by rearranging the elements in such an order as to match the order of the column direction of the system matrix W (vectorization S128). This vector is referred to as first vector in this embodiment. The first vector has N×N elements because it has the value of a sinogram. The first vector can be said as a column vector obtained if the tomographic image is obtained and the system matrix W is operated on the vectorized version (column vector of N×N elements) of the tomographic image, as in Formula (1). The first vector is also denoted as X'. It should be noted that from irradiation and detection S124 to vectorization S128, quantization by analog-to-digital conversion of the signal, processing of the digital signal, and temporary storage of data for processing if necessary, can also be performed. It is sufficient to obtain data that can generate a sinogram, and it is not always necessary to display it, nor is it necessary to go through explicit data that may be considered a sinogram. If a first vector corresponding to a vectorized version of the sinogram is obtained based on the detection signal from the detection device 20, any processing that performs any equivalent processing from irradiation and detection S124 to vectorization S128 is also included in this embodiment. In order to realize a detection direction reflecting the above offset angle, it is not always necessary to set or control the detection operation of the device to deviate from a normal angle (e.g., a direction that the device has as a reference) by the amount of the offset angle, and this embodiment can be implemented by a mathematically equivalent process. For example, it is also useful for the present embodiment to keep the detection direction matched to a direction that the device has as a reference, and to perform a rotation transformation required for the coordinate axis for the image to realize the offset angle $\Delta\theta$ until reconstruction, and finally to apply a reverse rotation transformation of that amount to the reconstructed image.

Since the first vector X' satisfies the relationship of Formula (8) with the system matrix W, the relationship of Formula (9) is established using the discrete inverse Radon transform matrix $W^{-1}$, which is the inverse of the system matrix W. The second vector, which gives the reconstructed image, is obtained by the discrete inverse Radon transform process S132. This second vector is also referred to as X. The reconstructed image can be imaged by de-vectorizing the sequence of this second vector X, or through an inverse operation of vectorization (S134) in which an N×N pixels image is restored. This reconstructs the tomographic image for one slice, so that the slice position can be changed and the process can be performed if necessary.

The processing of this embodiment is divided into two sections, A and B, as shown in FIG. 8. Users who usually capture the reconstructed image perform section B of the processes leading from irradiation and detection step S124 to imaging step S134. That is, the user does not necessarily have to perform section A of the processes leading to the determination of the device configuration S102, the system matrix generation step S112 to the discrete inverse Radon transform matrix calculation step S116. Section A of the processes leading from the system matrix generation step S112 to the discrete inverse Radon transform matrix calculation step S116 are required for the processes that are handled by the equipment manufacturer, so to speak, in situations where the tomographic imaging system is fabricated, installed and maintained. If predetermined offset angles, $\Delta\theta$, are obtained, the user who intends to capture the reconstructed images only needs to use them for their own measurements. If data on the appropriate equipment information from section A are available, then the processing of the range of section B can be sufficiently performed using them.

It is noteworthy that the discrete Radon transform S126 to the imaging step S134 of section B is the reordering of matrices and vectors and the operation of the matrix multiplication, and that the processing that is problematic in terms of computational throughput, such as sequential approximation, for example, is not included in the range of the process. In this embodiment, the processing of section B, which is used in the user's normal imaging, can be performed with a sufficiently light computational burden simply by using the discrete inverse Radon transform matrix storage section 40, which is prepared by the processing of section A. This point brings a high degree of practicality to this embodiment. This is because the computational burden of the most frequent process of acquiring a tomographic image is very small. In particular, the method of this embodiment is extremely advantageous for applications in which many slices are repeatedly imaged to obtain a three-dimensional volume image. In addition to the fact that the repetition does not require processing in section A, the discrete Radon transformation S126 to imaging S134 in section B is suitable for many-core processors such as general-purpose computing on graphics processing units (GPGPU), so that the processing speed can be expected to increase in the future.

In addition, the system matrix W and the inverse matrix $W^{-1}$ of the system matrix W, which reflect the geometric aspects, are included only in the section A of the processing leading to the system matrix generation step S112 to the discrete inverse Radon transform matrix calculation step S116, and are separated from the section B for measurement (FIG. 4). The problem of convergence and the noise aspect for measurement are inherently separated from the problem of convergence when utilizing iteration for algebraic methods. This has an additional advantage in that, in this embodiment, the phenomenon caused by approximate solutions that are unrelated to noise is less likely to occur, and various noise reduction processes commonly employed in image processing are more likely to be effective as intended.

2.3 Determination of the Offset Angle $\Delta\theta$ to Give a Regular System Matrix As discussed above in the overview, the finding of the discrete inverse Radon transform matrix $W^{-1}$ for an inverse of the system matrix W is dependent on the appropriateness of the offset angle $\Delta\theta$. The offset angle $\Delta\theta$ is determined in a process not illustrated in FIG. 8. The process of determining the offset angle $\Delta\theta$ in this embodiment is not limited insofar as it gives a regular system matrix as a result.

The procedure to search for offset angles $\Delta\theta$ is performed as shown in FIG. 9. First of all, as explained through FIG. 7C, we can expect to find it in a few steps for realistic values of resolution N if we use an initial value around $\pm\pi/4$ (rad)($\pm 45°$) for the search. After setting the initial value of the offset angle $\Delta\theta$, the system matrix W is calculated (S42). Then, it is determined whether a rank that has been calculated for the system matrix W corresponds to N×N or not (S44). If there is no match, the value of the offset angle $\Delta\theta$ is modified (S46), whereas if there is a match, then the value obtained is set to the offset angle $\Delta\theta$ as it is (S48). Then it returns to the generation of the system matrix W (S42). By this process, it is possible to determine the system matrix W and the offset angle $\Delta\theta$ thereof, with which we can obtain the inverse matrix with certainty. The subsequent processing shown in FIG. 9 is unnecessary once the resolution N, which is the number of detection elements 22 of the detection device 20, is determined as well as the offset angle $\Delta\theta$. Therefore, the user does not need to determine the offset angle $\Delta\theta$ every time the imaging is performed. Even if the value of the offset angle $\Delta\theta$ given for each resolution N is obtained by some means and used as it is, there is no obstacle to the implementation of the present embodiment.

2.4 Summary of Specific Structure

As shown in the above, the process of using the offset angle $\Delta\theta$ in the present embodiment provides high practicality for the process of tomographic image capture and acquisition. One of its advantages is that the processes of determining the offset angle $\Delta\theta$, generating the system matrix, and the inverse matrix thereof, can be performed separately from the process of the user's acquisition of the tomographic images. For this reason, there is no need to repeat the process of sequential approximation which is computationally intensive, in the embodiment of the present disclosure.

3. Implementation of the Embodiment

The present embodiment can be implemented on a tomographic imaging system or in a control and processing software for an existing tomographic imaging device.

3.1 Implementation on a Tomographic Imaging Device

The present embodiment of the tomographic imaging device 100 can acquire tomographic images of the same or better quality than those using conventional ART in a conventional tomographic imaging device as a tomographic imaging device 100 by performing the above-described processing mainly in the control device 150. The computational resources required for this process are also sufficiently practical and the processing is fast.

As shown in FIG. 10, the system matrix generation unit 162 and the inverse matrix calculation unit 166 perform the system matrix generation step S112 and the discrete inverse Radon transform matrix calculation step S116, respectively. Similarly, the operation control unit 174, the discrete Radon transform processing unit 176, the vectorization processing unit 178, the discrete inverse Radon transform processing unit 182, and the image data generation unit 184 perform the irradiation and detection step S124, the discrete Radon transform S126, the vectorization S128, the discrete inverse Radon transform processing S132, and the imaging step S134 respectively. In its operation, the discrete inverse Radon transform matrix storage unit 40 and the system matrix storage unit 60 are also utilized. In addition, the irradiation and detection step S124, the discrete Radon transformation S126, and the vectorization step S128 can be carried out by functional unit that can perform a combination of these processes in function, just as the irradiation and detection S124 to the vectorization S128 can be carried out by corresponding processes. Furthermore, the control device 150 can be implemented in various forms, such as one that primarily performs the processing of section A, or conversely, one that primarily performs the processing of section B, as necessary, since the functional units required for the processing of section A and section B are clearly separated. Specific examples of tomographic imaging devices include X-ray CT scanners, single photon emission computed tomography (SPECT), optical tomography, and optical CT devices.

3.2 Implementation in Computer Program

The entirety of the system can be implemented as the tomographic imaging device 100 with a tomographic imaging device equipped with an emission device 10 and a detection device 20 as an implementation of a computer program for example, in which the control device 150 in the tomographic imaging device 100 performs part of or all of the control steps, conversions, calculations, and other computational processes. Furthermore, the control device 150 in the tomographic imaging device 100 in the present embodiment can be made to perform only the processes in section B (FIGS. 8 and 9) at the time when the user captures the tomographic images.

4. Verification by Computer Simulation (Example)

Figure 11:
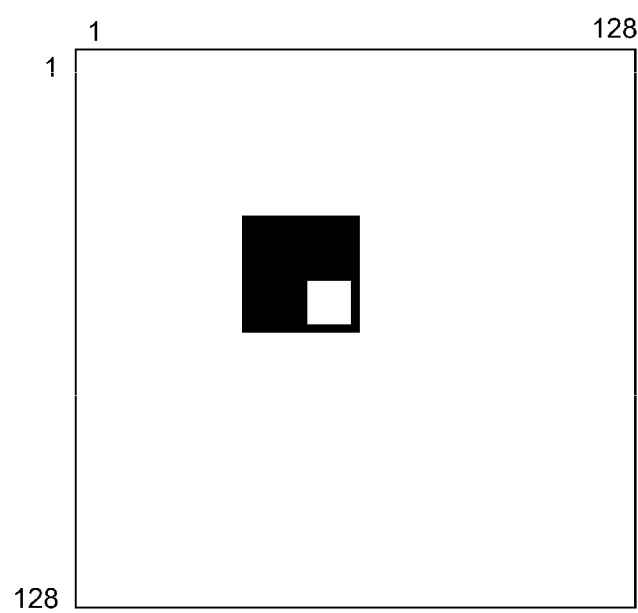
FIG. 11 indicates data for verification used for validation (numerical phantoms) in an example for the embodiment of the present disclosure.

The effectiveness of the reconstruction method according to the present embodiment was confirmed by computer simulation. The general processing, including the inverse Radon transform, including those of conventional methods for contrast, was performed using the mathematical processing software Mathematica (Wolfram Research, Inc., Champaign, Ill.) and the image processing software ImageJ (U.S. National Institutes of Health). A computer with an Intel Xeon E5 processor (3.5 GHz, 6-Core type) CPU and a 64 GB main memory was employed for the simulation process, including the processing of the control device 150 in this embodiment. FIG. 11 shows the validation data (numerical phantoms) used for verification (FIG. 11, referred to as an original image). In each figure, solid lines are added to the periphery of the image to distinguish it from the background, and numerical values indicating the first and last pixel numbers representing the coordinates of the pixels are shown on the top and left sides. The original image (numerical phantom) is numerical data artificially given for simulating the structure of attenuation rate in a cross section of an object in a computer simulation, and can be represented as N=128, or 128×128 image with pixels corresponding to spatial positions. In FIG. 11, the region of strong absorption is depicted darkly and the region of weak absorption is depicted brightly. In the computer simulation, the operation of the irradiation and detection S124 by the tomographic imaging device 100 was also simulated, and numerical data corresponding to the measured values were obtained by calculation. In the present method, a sinogram acquired in the N directions (128 directions) can be captured (not shown).

As a validation of this embodiment, the offset angle $\Delta\theta$ was set to 0.7770 (rad)(44.5188°) as shown in Table 1, when the resolution N was set to 128. The reconstructed images shown in FIG. 12A, FIG. 12B, and FIG. 12C were obtained based on the present embodiment (FIG. 12A), by using the Hann filter in the conventional FBP method (FIG. 12B), and by performing 30 sequential approximation calculations (ML-EM method) as a conventional algebraic reconstruction method (FIG. 12C). In applying the FBP and ML-EM methods, we shifted the projections corresponding to the offset angle $\Delta\theta$ (32 projections) in the sinogram obtained by this method to cancel the rotation of the image (angle $\Delta\theta$) that occurs in the final reconstructed image. Although the reconstructed images in this embodiment are obtained in the range of 128×128 pixels, these reconstructed images are shown only in the range of 91×91 pixels. This is because the area where the reconstructed image can be obtained by simulation using the FBP method is a circular region with a diameter of 128 pixels, and a square region roughly inscribed in the circle can be compared.

Figure 12A:
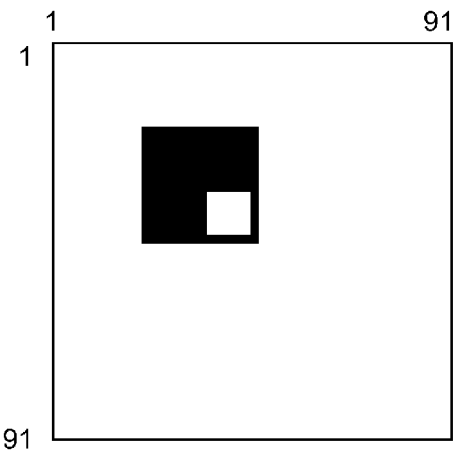
FIG. 12A, FIG. 12B, and FIG. 12C indicate the reconstructed images obtained in an example for the embodiment of the present disclosure, one obtained by the present embodiment (FIG. 12A), one obtained by using a Hann filter in a conventional FBP method (FIG. 12B), and one obtained by performing 30 sequential approximation calculations (ML-EM method) as a conventional algebraic reconstruction method (FIG. 12C).
Figure 12B:
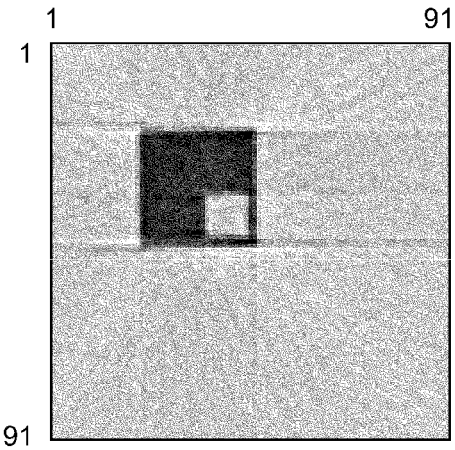
Figure 12C:
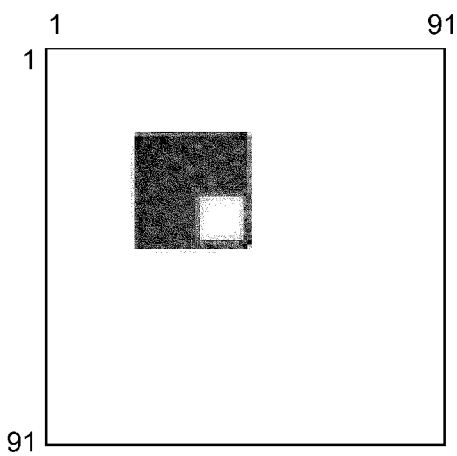

As it is clear by comparing FIG. 11 and FIG. 12A, a reconstructed image with extremely high reproducibility was obtained in the present embodiment. This is an advantage of this embodiment, which is supported by the fact that the discrete inverse Radon transform matrix $W^{-1}$ is an algebraic exact solution, unlike the conventional Hann filtered FBP method (FIG. 12B) and the ML-EM method (FIG. 12C), which has been confirmed through the high reproducibility of the image itself.

5. Variations in Image Reconstruction Methods

In the image reconstruction method described above, the image reconstruction was performed by actually calculating the inverse matrix $W^{-1}$ from the regular system matrix W under the guarantee that the system matrix W is regular and has an inverse matrix by adopting an appropriate offset angle. In the present disclosure, it is possible to utilize a pseudo-inverse of a regular system matrix W by employing a similar appropriate offset angle for an additional image reconstruction technique.

The pseudo-inverse matrix is calculated for this additional image reconstruction method, e.g., by a method of singular value decomposition (SVD). For example, a Moore-Penrose type inverse matrix can be generated by a singular value decomposition on a square matrix and is an example of a useful pseudo-inverse matrix for this additional image reconstruction method.

In the embodiment of the present disclosure, Formula (8) above is utilized in both the image reconstruction method described above and this additional image reconstruction method. In this case, it is guaranteed that the system matrix W is regular, i.e., it has an inverse matrix, if an appropriate offset angle is selected. The image reconstruction method described above was to obtain the discrete inverse Radon transform matrix $W^{-1}$, which is the inverse of this regular system matrix W, and to implement the image reconstruction according to Formula (9).

This additional image reconstruction method is equivalent until Formula (8), but instead of Formula (9), the image reconstruction is carried out according to $$X = W_p^{-1} X' \qquad (10)$$

Here, $W_p^{-1}$ is the pseudo-inverse matrix of the system matrix W. In other words, even if the pseudo-inverse matrix $W_p^{-1}$, which is an approximate inverse matrix, is used instead of using the inverse of the system matrix W, where the existence of the inverse matrix is guaranteed by adopting an appropriate offset angle, the image reconstruction can be performed in this additional image reconstruction method.

The process for this additional image reconstruction method will be described with the elements of FIGS. 8-10 appended as necessary. In the first place, an appropriate offset angle is adopted for the direction of detection in the N direction (FIG. 8, S104). Then, the system matrix W is calculated (S112). The fact that this system matrix W is regular is confirmed by calculating its rank (FIG. 9). Furthermore, the Moore Penrose type inverse of the system matrix W in question is derived to calculate the pseudo-inverse matrix $W_p^{-1}$, which is the discrete inverse Radon transform matrix $W^{-1}$. Therefore, the pseudo-inverse matrix is calculated in the discrete inverse Radon transform matrix calculation step S116 in FIG. 8, and the pseudo-inverse matrix is stored in the discrete inverse Radon transform matrix storage unit 40 (FIG. 8, FIG. 10).

Next, data is acquired from the target object in the above N detection directions (S122, S124). Then, the first vector X' corresponding to the sinogram is generated (S126, S128). Thereafter, the second vector X is calculated by the pseudo-inverse matrix $W_p^{-1}$ (S132), and furthermore, the reconstructed image is obtained by the de-vectorization process (S134). The calculation of the pseudo-inverse matrix $W_p^{-1}$ can be performed by setting an appropriate tolerance, which will be described below. In this way, an additional image reconstruction method using the pseudo-inverse matrix $W_p^{-1}$ can be used to produce a reconstructed image with good quality.

The calculation of the pseudo-inverse matrix $W_p^{-1}$ is typically carried out by setting an appropriate tolerance value. The tolerance value is expressed in terms of the ratio of the criterion value for excluding singular values in the singular value sequence against the maximum of singular values in the process of generating a pseudo-inverse matrix through approximation of the singular value decomposition. For example, if ⅕ is the tolerance value, the pseudo-inverse matrix is calculated from the singular value decomposition matrix by replacing the singular values that have values less than ⅕ of the maximum singular value by 0. When the inventors examined the example with N=64, the reconstructed image did not form a recognizable image when the tolerance is set to 1/1. As the tolerance is reduced, the reconstructed image increases in resolution, but is relatively stable after 1/13.

As described above, even for system matrices W, which are guaranteed to have an inverse matrix with regularity by adopting an appropriate offset angle, the use of pseudo-inverse matrices can produce a reconstructed image of sufficient quality.

It should be noted that, in general, the smaller the tolerance value for the pseudo-inverse, the closer the calculated pseudo-inverse is to the inverse matrix and the higher the resolution of the reconstructed image becomes. However, in measurements using a realistic measurement device, smaller values do not necessarily result in better reconstructed images. This is because there are various disturbing factors that cannot be attributed to geometric factors. For example, noise in the detection signal, beam instability, beam scattering, and image characteristics of the device itself remain as disturbing factors in current measurement devices. Normally, the imaging performance of the whole system, which reflects all these factors, is evaluated by, for example, the modulation transfer function (MTF), which indicates the resolution characteristics, and the Wiener spectrum, which is a measure of the image granularity. By using a predetermined tolerance value greater than 0 in the present additional image reconstruction method, a filter operation to exclude disturbing factors other than geometric factors is achieved. Since this filter operation can easily adjust its effect by increasing or decreasing the tolerance value, the filter operation can be useful in creating a necessary reconstruction image according to the image characteristics of interest, such as whether to focus on resolution or quantification.

6. Variations

This embodiment can be implemented in various forms other than those described above, regardless of whether it is implemented with a tomographic image data acquisition method, a tomographic image data acquisition device or a computer program for that purpose. For example, it is not required for the user to be involved in the process of determining the device parameter information in section A in FIGS. 8 and 10, and it is also easy to modify the embodiment in such a way that the user is involved only in obtaining the measurement information in section B. Furthermore, for example, when provided by a computer program for implementing the present embodiment, it is also possible to implement the present embodiment by adopting existing or already installed hardware for irradiation and detection and newly incorporating the above-mentioned processes into the computer program for controlling it. Thus, the method of this embodiment can be implemented through various modes of implementation.

In addition to the variations of the embodiment, another variation of the details of the process is also a part of this embodiment. One example of this is a method of determining the contribution of a pixel with respect to the beam 4 to a detection element 22 described with reference to FIG. 3A and FIG. 3B. In addition to the method of using the area of the patterned area in FIG. 3A and FIG. 3B as the contribution, other practical methods may be employed in this embodiment as well. For example, instead of the area, it is also advantageous to have a weight depending on the length of the sweep, or to adopt Siddon's algorithm, which efficiently evaluates the length of the sweep, to determine the above contribution (Non-Patent Document 3). Furthermore, it is also advantageous to utilize the method of Sunnegardh and Danielson, which is capable of anti-aliasing to achieve a higher image quality (Non-Patent Document 4).

Furthermore, although the explanations from FIG. 1A and FIG. 1B and thereafter have been explained by the operation of one example tomographic imaging device 100, the present embodiment is not necessarily limited to ones employing the emission device 10. This embodiment can be similarly applied to other techniques such as SPECT (single-photon emission tomography), in which tomographic imaging of an object is performed without the use of an emission device.

In the above description, the embodiment of the present disclosure has been described specifically. Any description in this Specification is for the purpose of explaining the present disclosure, therefore the scope of the disclosure of this disclosure should be determined based on recitations of the claims. Furthermore, other variation based on any combination of the embodiment is included in the present disclosure, which variation should be also within a scope of the present disclosure.

INDUSTRIAL APPLICABILITY

The present disclosure can be applied to any tomographic imaging methods where the waves or particles are transmitted through an object itself, e.g., by, for example, being irradiated onto the object, such as X-ray CT scanners, Single Photon Emission Computed Tomography (SPECT), Optical Tomography, and optical CT devices.

REFERENCE SIGNS LIST

100 Tomographic imaging device (tomographic image data acquisition device)
2 Object.
4 Beam
10 Emission device
20 Detection device
22 Detection element
40 Discrete inverse Radon transform matrix storage unit
60 System matrix storage unit
150 Control device
162 System matrix generation unit.
166 Inverse matrix calculation unit
174 Operation control unit
176 Discrete Radon transform processing unit
178 Vectorization processing unit
182 Discrete inverse Radon transform processing unit
184 Image data generation unit The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for acquiring image data comprising:
disposing an object in a detection range of a detection device having N detectors (N is a positive integer) arranged in at least one row;
detecting in a detection operation an intensity value for each of the detection detectors by receiving transmitted waves or particles by each of the detectors are performed, where the waves or particles are detectable by the detection device, in each of relative detection directions for the waves or particles viewed from the object, while irradiation of the waves or particles toward the detection device by an irradiator is performed, or while the waves or particles generated without the irradiator are transmitted through each part of the object;
obtaining a first vector with N×N elements from a detection signal by the detection device in the detection operation, wherein the elements of the first vector corresponding to those obtained by vectorizing a sinogram with N rows and N columns, each row and each column of which are associated with each detection direction and each of the detectors, respectively;
operating a discrete inverse Radon transform matrix to the first vector to obtain a second vector having N×N elements; and
obtaining image data by de-vectorizing the second vector, for a two-dimensional tomographic image of N pixels×N pixels having a pixel arrangement in which each pixel is addressed by two-dimensional coordinates where two coordinate axes are defined for the object with a common pitch in vertical and horizontal axes, wherein
the each of the detection directions in the detecting in the detection operation being an angle sampling direction corresponding to each angle increment equally dividing an angle scan range into N divisions for reconstructing the two-dimensional tomographic image, wherein one of two directions adjacent to each of two boundaries is offset from one of the coordinate axes and the offset angle is greater than 0° and less than 90° or greater than −90° and less than 0°.

2. The method for acquiring tomographic image data according to claim 1, wherein each of the detection directions is neither perpendicular nor orthogonal to any of the coordinate axes.

3. The method for acquiring tomographic image data according to claim 2, further comprising:
obtaining the discrete Inverse Radon transform matrix by calculating an inverse matrix of a system matrix having column- or row vectors of N×N elements, each of which elements has a weight value indicative of contribution of each pixel of the two-dimensional tomographic image to a path of a portion of the waves or particles, the path going toward each of N detectors, which column- or row vectors are arranged in a column or a row direction according to each of the N detection directions while being associated with the pixels of the two-dimensional tomographic image.

4. The method for acquiring tomographic image data according to claim 3, further comprising:
determining that the system matrix is a regular matrix.

5. The method for acquiring tomographic image data according to claim 4, comprising:
repeating, until the system matrix becomes the regular matrix,
the determining that the system matrix is the regular matrix ; and
resetting an offset angle in which the offset angle is changed in a case the system matrix is not the regular matrix.

6. The method for acquiring tomographic image data according to claim 4, wherein the determining that the system matrix is the regular matrix includes determining a rank for the system matrix, and determining whether or not the rank matches N×N.

7. The method for acquiring tomographic image data according to claim 2, further comprising:
  obtaining the discrete Inverse Radon transform matrix by calculating a pseudo inverse matrix of a system matrix having column- or row vectors of N×N elements, each of which elements has a weight value indicative of contribution of each pixel of the two-dimensional tomographic image to a path of a portion of the waves or particles, the path going toward each of N detectors, which column- or row vectors are arranged in a column or a row direction according to each of the N detection directions while being associated with the pixels of the two-dimensional tomographic image.

8. The method for acquiring tomographic image data according to claim 7, further comprising:
  determining that the system matrix is a regular matrix.

9. A tomographic image data acquisition device comprising:
  a detection device having N detectors arranged in at least one row where N is an integer of 1 or more; and
  a controller that controls the detection device so that the detection device detects waves or particles after the waves or particles are transmitted each part of an object disposed in a detection range of the detection device by each of the detectors in a detection direction, wherein the detection direction is changed with respect to the object while irradiation of the waves or particles toward the detection device by an irradiator is performed, or while the waves or particles generated without the irradiator are transmitted through each part of the object and wherein the waves or particles are detectable by the detection device,
  wherein the tomographic image data acquisition device further comprises:
    a discrete inverse Radon transform matrix storage for storing a discrete inverse Radon transform matrix, and
  wherein the controller comprises:
    a discrete Radon transform processor for changing a relative detection direction for the waves or particles viewed from the object and for making the detection device output a detection signal for a sinogram with N rows and N columns, each row and each column of which are associated with each detection direction and each of the detectors, respectively;
    a vectorization processor for obtaining from the detection signal a first vector having N×N elements corresponding to those obtained by vectorizing the sinogram;
    a discrete inverse Radon transform processor for obtaining a second vector having N×N elements by operating the discrete inverse Radon transform matrix to the first vector; and
    an image data generator, by de-vectorizing the second vector, for obtaining image data for a two-dimensional tomographic image of N pixels×N pixels having a pixel arrangement in which each pixel is addressed by two-dimensional coordinates where two coordinate axes are defined for the object with a common pitch in vertical and horizontal axes,
  wherein the controller controls the detection device such that the detection device performs detection in each of the detection directions, which is an angle sampling direction corresponding to each angle increment equally dividing an angle scan range into N divisions for reconstructing the two-dimensional tomographic image, and
  wherein one of two directions adjacent to each of two boundaries is offset from one of the coordinate axes and the offset angle is greater than 0° and less than 90° or greater than −90° and less than 0°.

10. The tomographic image data acquisition device according to claim 9, wherein each of the detection directions is neither perpendicular nor orthogonal to any of the coordinate axes.

11. The tomographic image data acquisition device according to claim 9, further comprising:
  a system matrix storage,
  wherein the controller further comprises:
    a system matrix generator for obtaining a system matrix having column- or row vectors of N×N elements, each of which elements has a weight value indicative of contribution of each pixel of the two-dimensional tomographic image to a path of a portion of the waves or particles, the path going toward each of N detectors, which column- or row vectors are arranged in a column or a row direction according to each of the N detection directions while being associated with the pixels of the two-dimensional tomographic image and for storing the system matrix into the system matrix storage; and
    an inverse matrix calculator for obtaining the discrete Inverse Radon transform matrix by calculating the inverse matrix of the system matrix and for storing the inverse matrix into the discrete Inverse Radon transform matrix storage.

12. A control program for an acquisition device of tomographic image data, the acquisition device having:
  a detection device having N detectors arranged in at least one row where N is a positive integer, and
  a controller that controls the detection device so that the detection device detects waves or particles after the waves or particles are transmitted each part of an object disposed in a detection range of the detection device for the waves or particles by each of the detectors in a detection direction, wherein relative detection direction for the waves or particles is changed with respect to the object while irradiation of the waves or particles toward the detection device by an irradiator is performed, or while the waves or particles generated without the irradiator are transmitted through each part of the object and wherein the waves or particles are detectable by the detection device,
  wherein the control program makes the controller to perform:
    processing a discrete Radon transform, in which a relative detection direction for the waves or particles viewed from the object is changed, for making the detection device output a detection signal for a sinogram with N rows and N columns, each row and each column of which are associated with each detection direction and each of the detectors, respectively;
    obtaining from the detection signal a first vector having N×N elements corresponding to those obtained by vectorizing the sinogram;
    retrieving a discrete inverse Radon transform matrix from a discrete inverse Radon transform matrix storage and obtaining a second vector having N×N elements by operating the discrete inverse Radon transform matrix to the first vector; and obtaining image data by de-vectorizing the second vector, for obtaining image data for a two-dimensional tomographic image of N pixels×N pixels having a pixel arrangement in which each pixel is addressed by two-dimensional coordinates where two coordinate axes are defined for the object with a common pitch in vertical and horizontal axes, wherein the controller controls the detection device such that the detection device performs detection in each of the detection directions, which is an angle sampling direction corresponding to each angle increment equally dividing an angle scan range into N divisions for reconstructing the two-dimensional tomographic image, and wherein one of two directions adjacent to each of two boundaries is offset from one of the coordinate axes and the offset angle is greater than 0° and less than 90° or greater than −90° and less than 0°.

13. The control program according to claim 12, wherein each of the detection directions is neither perpendicular nor orthogonal to any of the coordinate axes.

14. The control program according to claim 13, further making the controller to perform:

obtaining the discrete Inverse Radon transform matrix by calculating an inverse matrix of a system matrix having column- or row vectors of N×N elements, each of which elements has a weight value indicative of contribution of each pixel of the two-dimensional tomographic image to a path of a portion of the waves or particles, the path going toward each of N detectors, which column- or row vectors are arranged in a column or a row direction according to each of the N detection directions while being associated with the pixels of the two-dimensional tomographic image and storing the discrete Inverse Radon transform matrix into the discrete Inverse Radon transform matrix storage.

15. The control program according to claim 13, further making the controller to perform:

obtaining the discrete Inverse Radon transform matrix by calculating a pseudo inverse matrix of a system matrix having column- or row vectors of N×N elements, each of which elements has a weight value indicative of contribution of each pixel of the two-dimensional tomographic image to a path of a portion of the waves or particles, the path going toward each of N detectors, which column- or row vectors are arranged in a column or a row direction according to each of the N detection directions while being associated with the pixels of the two-dimensional tomographic image and storing the discrete Inverse Radon transform matrix into the discrete Inverse Radon transform matrix storage.

* * * * *